(12) United States Patent
Choe et al.

(10) Patent No.: US 10,307,075 B2
(45) Date of Patent: Jun. 4, 2019

(54) EXTERNAL STANDARD REFERENCE SYSTEM OF TYPE INSERTED INTO COIL OF HUMAN MAGNETIC RESONANCE IMAGING EQUIPMENT

(71) Applicant: The Catholic University of Korea Industry-Academic Cooperation Foundation, Seoul (KR)

(72) Inventors: Bo-Young Choe, Seoul (KR); Kyu-Ho Song, Gyeonggi-do (KR); Do-Wan Lee, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 467 days.

(21) Appl. No.: 14/872,805

(22) Filed: Oct. 1, 2015

(65) Prior Publication Data

US 2017/0049354 A1 Feb. 23, 2017

(30) Foreign Application Priority Data

Aug. 18, 2015 (KR) ........................ 10-2015-0116115

(51) Int. Cl.
| | |
|---|---|
| *A61B 5/055* | (2006.01) |
| *G01R 33/58* | (2006.01) |
| *G01R 33/46* | (2006.01) |
| *G01R 35/00* | (2006.01) |
| *A61B 5/00* | (2006.01) |

(52) U.S. Cl.
CPC ............ *A61B 5/055* (2013.01); *A61B 5/0042* (2013.01); *G01R 33/58* (2013.01); *G01R 35/00* (2013.01); *G01R 33/46* (2013.01)

(58) Field of Classification Search
None
See application file for complete search history.

(56) References Cited

U.S. PATENT DOCUMENTS

| | | | | | |
|---|---|---|---|---|---|
| 4,233,507 | A | * | 11/1980 | Volz ....................... | A61B 6/032 378/18 |
| 4,985,906 | A | * | 1/1991 | Arnold .................. | A61B 6/583 378/18 |
| 5,034,969 | A | * | 7/1991 | Ozaki .................... | A61B 6/583 378/162 |

* cited by examiner

*Primary Examiner* — Tse W Chen
*Assistant Examiner* — Jason M Ip
(74) *Attorney, Agent, or Firm* — Hoffmann & Baron, LLP (57) ABSTRACT

The present invention relates to an external standard reference system of a type inserted into the coil of a human magnetic resonance imaging equipment, and more specifically, to a system capable of analyzing metabolic components (quantity of metabolites) in a human body without an error and a limited range using an external standard reference analysis method, in order to enhance accuracy of diagnosis by utilizing magnetic resonance spectroscopy of the human magnetic resonance imaging equipment. A system for evaluating performance of magnetic resonance spectroscopy includes an outer container for inserting an RF coil and provided with a plurality of holes; a plurality of inner containers arranged to be inserted into the plurality of holes respectively and capable of being filled with metabolites different from each other in at least a type or a concentration; and a frame for fixing a head of an object arranged inside the outer container.

16 Claims, 4 Drawing Sheets

EXTERNAL STANDARD REFERENCE SYSTEM OF TYPE INSERTED INTO COIL OF HUMAN MAGNETIC RESONANCE IMAGING EQUIPMENT

CROSS REFERENCE TO RELATED APPLICATION

This application claims benefit of Korean Patent Application No. 10-2015-0116115 filed on Aug. 18, 2015, the contents of which are incorporated herein by reference in their entirety.

BACKGROUND OF THE INVENTION

Field

The present invention relates to an external standard reference system of a type inserted into the coil of a human magnetic resonance imaging equipment, and more specifically, to a system capable of analyzing metabolic components, i.e., quantity of metabolites, in a human body without an error and a limited range using an external standard reference analysis method, in order to enhance accuracy of diagnosis by utilizing magnetic resonance spectroscopy of the human magnetic resonance imaging equipment.

Related Art

Magnetic Resonance Imaging (MRI) is a typical imaging technique capable of measuring brain functions of a human body, and Magnetic Resonance Spectroscopy (MRS), capable of detecting chemical components of a brain tissue by providing structural images, which gives various image contrasts and is used in a variety of ways.

The Magnetic Resonance Imaging uses principles of nuclear magnetic resonance as one of the imaging techniques. That is, if a human body is put into a magnetic resonance imaging apparatus generating a magnetic field and a high frequency is generated, the hydrogen nucleus of the human body resonates, and a magnetic resonance image can be created by measuring a difference of signals generated at this point and reconfiguring a result of the measurement into an image through a computer.

The magnetic resonance imaging is characterized in that it does not do any harm to a human body unlike the X-ray computed tomography (CT) which uses X-ray beams and thus is harmful to a human body, and the MRI is advantageously free from directions unlike the CT in which an axial image is the main image.

A low field or high field human magnetic resonance imaging equipment generally uses an 8-channel, 16-channel, or 32-channel coil dedicated to a brain and a general body coil for acquiring whole body images.

Generally, in order to further precisely and accurately analyze image reading and image acquisition, human magnetic resonance images and magnetic resonance spectroscopy spectra are acquired using a protocol proposed in the prior art.

Currently, an internal standard reference analysis method is used when magnetic resonance spectroscopy of a brain or magnetic resonance spectroscopy of other tissues is performed.

The internal standard reference analysis method is a method of acquiring information with reference to signals of water as a standard and performs an absolute concentration evaluation and a relative concentration evaluation using concentration of metabolites acquired through the method.

Since water is referenced as a standard in this method, there are a lot of restrictions, and, in addition, it is difficult to estimate efficiency of water suppression in existing equipment.

That is, although a coil dedicated to a human brain is developed in the current method, there is something insufficient in temporal efficiency and diagnostic accuracy of the magnetic resonance spectroscopy, which are important in a diagnosis region, and it is limited to an internal standard reference analysis method and a substitute phantom external standard reference analysis method.

Accordingly, an external standard reference analysis method and system using magnetic resonance spectroscopy is required, and it is configured by developing a container capable of referencing a metabolite as a standard and inserting the container into a coil.

SUMMARY OF THE INVENTION

Therefore, the present invention has been made in view of the above problems, and it is an object of the present invention to provide an external standard reference system of a type inserted into the coil of human magnetic resonance imaging equipment. Specifically, an object of the present invention to provide a user with a system capable of analyzing metabolic components, i.e., quantity of metabolites, in a human body without an error and a limited range using an external standard reference analysis method, in order to enhance accuracy of diagnosis by utilizing magnetic resonance spectroscopy of the human magnetic resonance imaging equipment.

The technical problems to be solved by the present invention are not limited to the technical problems mentioned above, and unmentioned other technical problems may be clearly understood by those skilled in the art from the following description.

To accomplish the above object, according to one aspect of the present invention, there is provided a system for evaluating performance of magnetic resonance spectroscopy, the system including: an outer container provided with an opening and a plurality of holes surrounding the opening, the opening to receive a head of an object; a plurality of inner containers to be inserted into the plurality of holes respectively and filled with metabolites; and a frame to fix the head of the object received inside the opening of the outer container, wherein the metabolites filled in the inner containers may be different from each other in at least either a type or concentration.

In addition, vertical lengths of at least some of the plurality of inner containers may be different from each other.

In addition, the type and the concentration of at least some of the metabolites filled in the plurality of inner containers may be replaceable.

In addition, performance of the magnetic resonance spectroscopy can be evaluated using the system in association with the following mathematical expression.

$$C_{mb} = C_{cp} \times (S_{mp}/S_{cp}) \times (f_{T1cp}/f_{T1mp}) \times (f_{T2cp}/f_{T2mp}) \times (N_{cp}/N_{mp})  \quad \text{Mathematical expression}$$

In the above mathematical expression, $C_{mb}$ denotes concentration of a human brain metabolite, $C_{cp}$ denotes concentration of a metabolite, $S_{mp}$ denotes a peak area of a brain metabolite, $S_{cp}$ denotes a peak area in an inner container, $f_{T1mp}$ denotes T1 relaxation time of a brain metabolite, $f_{T1cp}$ denotes T1 relaxation time of a metabolite in an inner container, $f_{T2mp}$ denotes T2 relaxation time of a brain metabolite, $f_{T2cp}$ denotes T2 relaxation time of a metabolite in an inner container, $N_{mp}$ denotes the number of transients acquired in a voxel for acquiring a brain metabolite, and $N_{cp}$ denotes the number of transients acquired in each voxel in an inner container.

In addition, the plurality of inner containers is six, and 12.5 mM of N-acetyl-aspartate [NAA], 12.5 mM of glutamate [Glu], 10 mM of creatine [Cr], 7.5 mM of myo-Inositol [mIns], 5.0 mM of lactate [Lac] and 3.0 mM of choline [Cho] may be contained in each of the six inner containers.

The present invention may provide a user with an external standard reference system of a type inserted into the coil of human magnetic resonance imaging equipment.

Specifically, the present invention may provide a user with a system capable of analyzing metabolic components, i.e., quantity of metabolites, in a human body without an error and a limited range using an external standard reference analysis method, in order to enhance accuracy of diagnosis by utilizing magnetic resonance spectroscopy of the human magnetic resonance imaging equipment.

Since the external standard reference system of a type inserted into the coil of a human magnetic resonance imaging equipment according to the present invention quantitatively acquires a brain metabolite and, furthermore, simultaneously acquires the evaluation and analysis functions while minimizing artifacts by selecting an accurate voxel position when a spectrum is acquired using magnetic resonance spectroscopy, there is an effect of acquiring the evaluation and analysis functions in a short time and improving diagnostic reliability of the magnetic resonance spectroscopy.

The technical problems to be solved by the present invention are not limited to the technical problems mentioned above, and unmentioned other technical problems may be clearly understood by those skilled in the art from the following description.

DETAILED DESCRIPTION

Generally, magnetic resonance spectroscopy is a technique capable of analyzing metabolites of a human body, and it is used in analyzing components of a material or a molecular structure.

In addition, the magnetic resonance spectroscopy is a method of precisely observing changes of magnetic resonance signals (frequencies) with respect to an applied RF pulse and quantitatively analyzing a structure, components, states, and the like of a certain inspection target when the inspection target is placed in a magnetic field.

Accordingly, biochemical information according to mechanical operation of a metabolite can be obtained from a given sample in a method harmless to a measurement target, and such information is determined according to the type of molecular components in the sample.

Although such magnetic resonance spectroscopy is known as an outstanding technique among the analysis methods used in the chemical and biochemical field and actively utilized even in the clinical field since 1990, it is mostly used in the field of neuroscience aiming at brains, i.e., an immobile organ, due to various technical restrictions.

In addition, the magnetic resonance spectroscopy distinguishes components of each element and determines a molecular structure in an analytical chemistry method using the fact that numerous protons existing in a human body respectively have a unique magnetic resonance frequency with a minute difference. A magnetic resonance spectroscopy data is expressed as a spectrum which displays various signal strengths using a reference compound providing a frequency of a reference point, and each peak position is expressed as a function of frequency (Hz). There is a minute difference in chemical and magnetic properties, i.e., a difference of magnetic field in a local region, between the protons constituting different tissues due to surrounding environments although the protons are like protons. Therefore, a spectrum can be easily distinguished since a resonance frequency also shows a minute difference. Such a minute difference of resonance frequency is referred to as a chemical shift, and a peak is shown at 4.7 ppm in the case of, for example, moisture.

Although the magnetic resonance spectroscopy can be embodied using magnetic resonance imaging equipment having a magnetic field strength of about 1.5 T and currently used in the clinic, it is effective to embody the magnetic resonance spectroscopy preferably using magnetic resonance imaging equipment having a magnetic field strength of 3T or higher, further preferably using magnetic resonance imaging equipment having a magnetic field strength of 7T or higher.

This is since that if a high field equipment is used, it is possible, compared to a case of using a low field equipment, to reduce the time creating an image since increased spin net magnetization can be obtained, easily acquire a small region of interest for obtaining an image of a local region from a magnetic resonance image, and improve resolution of a spectrum since a peak of a component in the spectrum appears to be extended according to the magnetic field strength in the case of the magnetic resonance spectroscopy.

A low field or high field human magnetic resonance imaging equipment generally uses an 8-channel, 16-channel, or 32-channel coil dedicated to a brain and a general body coil for acquiring whole body images.

Generally, in order to further precisely and accurately analyze image reading and image acquisition, human magnetic resonance images and magnetic resonance spectroscopy spectra are acquired using a protocol proposed in the prior art.

Currently, an internal standard reference analysis method is used when magnetic resonance spectroscopy of a brain or magnetic resonance spectroscopy of other tissues is performed.

The internal standard reference analysis method is a method of acquiring information with reference to signals of water as a standard and performs an absolute concentration evaluation and a relative concentration evaluation using concentration of metabolites acquired through the method.

Since water is referenced as a standard in this method, there are a lot of restrictions, and, in addition, it is difficult to estimate efficiency of water suppression in existing equipment.

That is, although a coil dedicated to a human brain is developed in the current method, there is something insufficient in temporal efficiency and diagnostic accuracy of the magnetic resonance spectroscopy, which are important in a diagnosis region, and it is limited to an internal standard reference analysis method and a substitute phantom external standard reference analysis method.

Accordingly, the present invention provides an external standard reference system of a type inserted into the coil of human magnetic resonance imaging equipment.

Specifically, an object of the present invention to provide a user with a system capable of analyzing metabolic components, i.e., quantity of metabolites, in a human body without an error and a limited range using an external standard reference analysis method, in order to enhance accuracy of diagnosis by utilizing magnetic resonance spectroscopy of the human magnetic resonance imaging equipment.

The external standard reference analysis method, which is a technique of the present invention, is a technique of measuring and acquiring data by accurately focusing on a desired metabolite of a human brain after distinguishing an absolute concentrate of the metabolite through the magnetic resonance spectroscopy of a human magnetic resonance system.

It is possible to further accurately analyze the data acquired through the magnetic resonance spectroscopy from the aspect of hardware of a human magnetic resonance imaging equipment, and a problem of diagnostic error of the internal standard reference analysis method performed with reference to the existing standard of water signal can be solved.

In addition, a laboratory, a company, or a school aiming at research and experiments on the insufficient part of a human diagnosis region uses magnetic resonance imaging equipment for studying small animals, as well as the human magnetic resonance imaging equipment, in a variety of fields.

Therefore, in the future, a technique of the magnetic resonance spectroscopy can be a technique which can be fundamentally advanced in a precise and accurate diagnosis region.

Particularly, magnetic resonance spectroscopy in magnetic resonance imaging equipment for small animals, as well as in human magnetic resonance imaging equipment, is a method of performing chemical clarification and quantification of a brain metabolite or a liver metabolite, and is used as a tool for providing information on metabolism in a living creature based on anatomical and histological images.

In addition, the magnetic resonance spectroscopy used in magnetic resonance imaging equipment is used as a method for discovery of early diagnosis, together with changes of metabolites in a cell, a tissue, or an organ on the basis of analysis of an acquired spectrum, evaluates effects of treatment when a disease is treated in a method of distinguishing difference of concentration of various metabolites of a human body, and uses a technique of early diagnosis accuracy based on changes of metabolites in the brain and the liver at a position occurring a disease for the purpose of research, and thus it is successfully used as a technique capable of performing a quantified chemical analysis on the metabolites in the brain and the liver.

Although a coil dedicated to a human brain has been developed based on the documents of the prior art, there is something insufficient in temporal efficiency and diagnostic accuracy of the magnetic resonance spectroscopy, which are important in a diagnosis region, and it is limited to an internal standard reference analysis method and a substitute phantom external standard reference analysis method.

Therefore, the present invention performs an external standard reference analysis method using magnetic resonance spectroscopy by developing a container capable of referencing a metabolite as a standard and inserting the container into a coil and is developed based on minimum and optimum temporal efficiency, which is the focal point of a diagnosis region.

Hereinafter, a system proposed in the present invention will be described in detail with reference to FIGS. 1 to 5C.

An object of the present invention is to provide a user with a system capable of analyzing metabolic components, i.e., quantity of metabolites, in a human body without an error and a limited range using an external standard reference analysis method, in order to enhance accuracy of diagnosis by utilizing magnetic resonance spectroscopy of the human magnetic resonance imaging equipment.

In addition, another object of the present invention is to provide a user with an insertion-type container, which can quantify a brain metabolite by changing a type and concentration of the brain metabolite and analyze metabolic components inside an outer container of the same size inserted into a coil.

Figure 1:
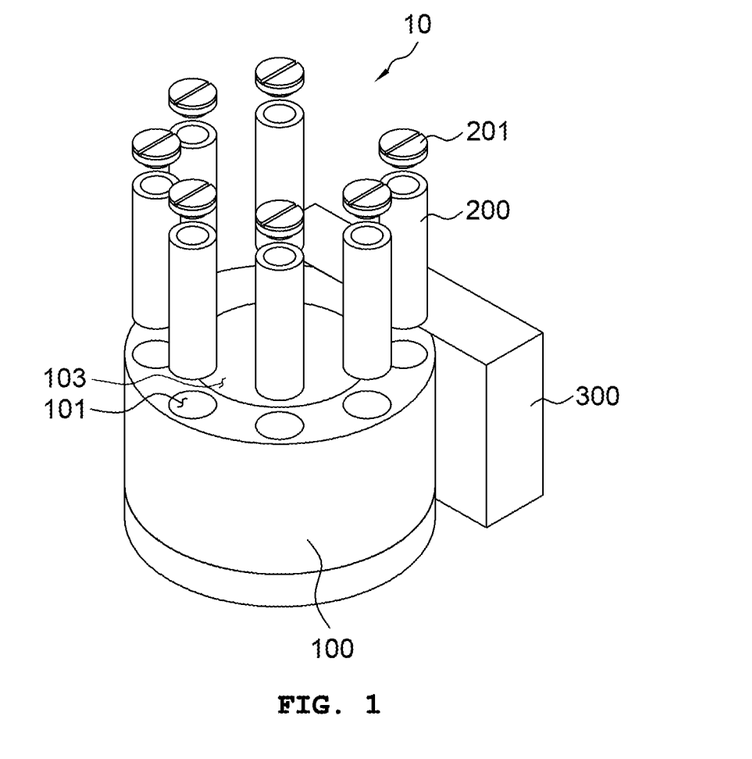
FIG. 1 is a view showing an external standard reference system of a type inserted into the coil of human magnetic resonance imaging equipment proposed in the present invention.
Figure 2A:
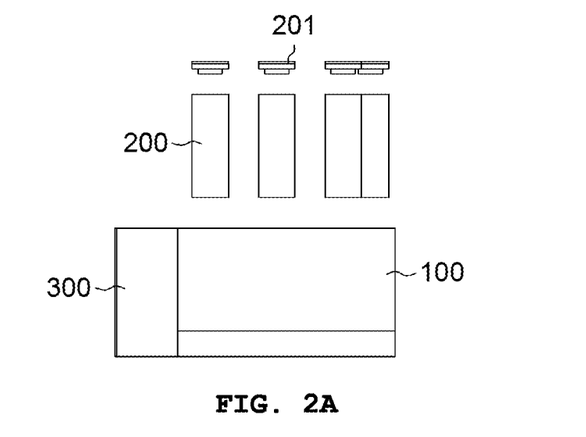
FIGS. 2A to 2C are views showing detailed components of the system shown in FIG. 1.
Figure 2B:
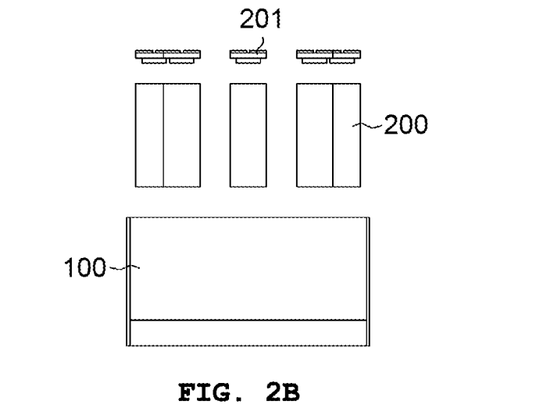
Figure 2C:
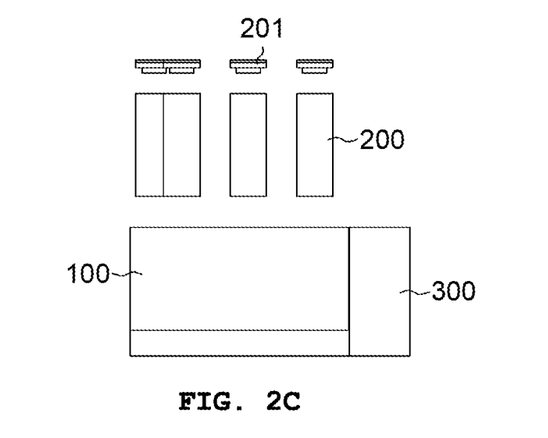

FIG. 1 is a view showing an external standard reference system of a type inserted into the coil of human magnetic resonance imaging equipment proposed in the present invention, and FIGS. 2A to 2C are views showing detailed components of the system shown in FIG. 1.

Figure 3A:
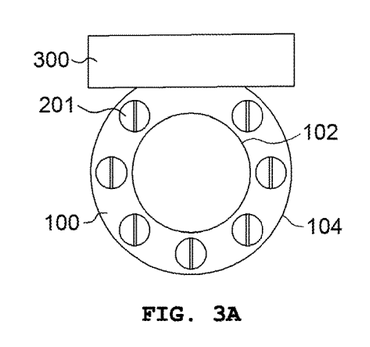
FIGS. 3A and 3B are views showing specific forms of an outer container, inner containers and a fixing frame included in the system shown in FIG. 1.
Figure 3B:
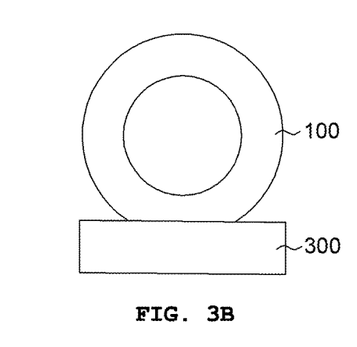
Figure 4A:
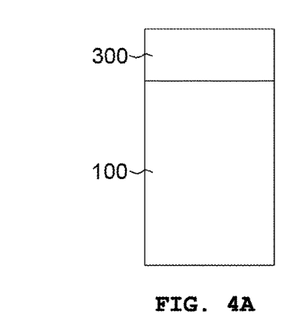
FIGS. 4A and 4B are other views showing specific forms of an outer container, inner containers, and a fixing frame included in the system shown in FIG. 1.
Figure 4B:
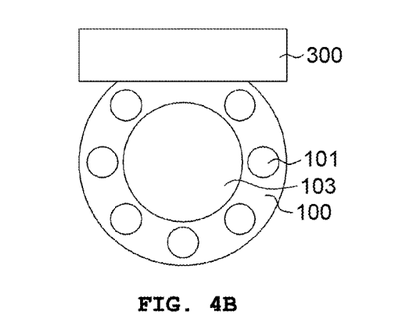

In addition, FIGS. 3A and 3B are views showing specific forms of an outer container, inner containers, and a fixing frame included in the system shown in FIG. 1, and FIGS. 4A and 4B are other views showing specific forms of an outer container, inner containers, and a fixing frame included in the system shown in FIG. 1.

Figure 5A:
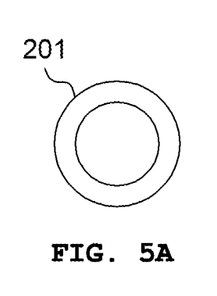
FIGS. 5A to 5C are views showing specific forms of an outer container and a cap included in the system shown in FIG. 1.
Figure 5B:
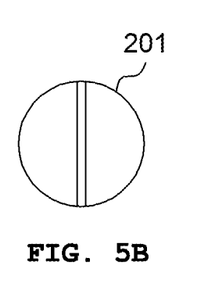
Figure 5C:
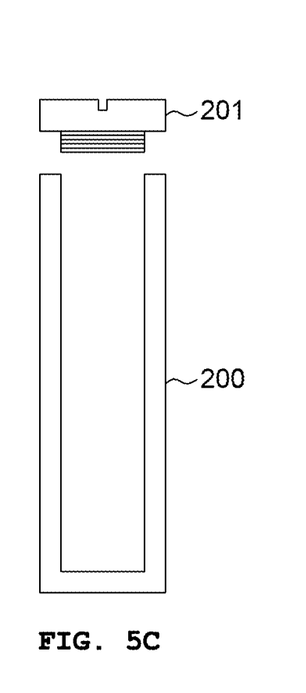

Finally, FIGS. 5A to 5C are views showing specific forms of an outer container and a cap included in the system shown in FIG. 1.

Basically, a system 10 proposed in the present invention includes a structure that may include an outer container 100 with an inside surface 102 defining an opening 103 and with an outside surface 104, and being provided with a plurality of holes 101 surrounding the opening 103, a plurality of inner containers 200 arranged to be inserted into the plurality of holes 101 respectively and filled with metabolites, and a frame 300 for fixing a head of an object received inside the opening 103 of the outer container 100.

Here, the most outstanding characteristic of the present invention is that the metabolites filled in the inner containers 200 may be different from each other in at least either the type or the concentration.

The system 10 proposed in the present invention is an integrated coil system 10, which can directly acquire a chemical shift spectrum without the need of changing containers of reference metabolites when magnetic resonance spectroscopy is performed, and separate and insert various containers ranging from a metabolite container of a small size to a metabolite container of a large scale.

Referring to FIG. 1, typically, inner containers 200 capable of filling four metabolites in total can be arranged in the integrated coil system, which is the outer container 100.

However, this is merely a simple example to which the present invention can be applied and may further include more or fewer inner containers 200.

Here, the inner containers 200 may be configured in different or same length respectively (length along the z-axis, in the direction inserted into the magnetic resonance imaging equipment when a person is diagnosed) to perform analysis on a spectrum together with magnetic resonance imaging.

In addition, since the frame 300 capable of fixing the head of a person is inserted into the coil of the outer container 100 to be arranged close to the container, artifacts required for movement of the head of the person can be reduced, and image and spectrum information can be efficiently provided.

In addition, referring to FIG. 1, basically, an RF coil is inserted into the opening 103 of the outer container 100, and the outer container 100 may be provided with a plurality of holes 101.

In addition, the inner containers 200 are arranged to be inserted into the plurality of holes 101 respectively and filled with metabolites, and lengths of the inner containers 200 and the metabolites filled therein may be different from each other.

In addition, caps 201 for tightly sealing the inner containers 200 may be separately provided.

Referring to FIGS. 2A to 2C, views of the integrated coil system 10, including the outer container 100, the inner containers 200, and the fixing frame 300, seen from the left side, rear side, and right side are shown.

In addition, referring to FIGS. 3A and 3B, views of the integrated coil system 10, combining the outer container 100, the inner containers 200, and the fixing frame 300, seen from the top and bottom sides are shown.

In addition, a form combining the outer container 100 and the fixing frame 300 is shown in FIG. 4A, and also a form including the holes 101 of the outer container 100 is shown in FIG. 4B.

In addition, a form of a cap 201 used for the inner container 200 is shown in FIGS. 5A and 5B, and a specific form of combining the cap 201 and the inner container 200 is shown in FIG. 5C.

If a test performed by the external standard reference system 10 of a type inserted into the coil of a human magnetic resonance imaging equipment of the present invention is compared with that of an existing standard reference system and magnetic resonance spectroscopy of the prior art, a high efficiency, above all, can be obtained in distinguishing an error in a movement and determining positional accuracy of a patient.

In addition, accurate measurement is allowed within a high field (1.5 Tesla or 3.0 Tesla) or ultrahigh field (7.0 Tesla) magnetic resonance imaging equipment.

In addition, performance evaluation and quality control of magnetic resonance imaging and magnetic resonance spectroscopy can be acquired in a considerably short time.

Furthermore, when the system of the present invention is applied, positional accuracy is corrected after an inaccurate acquisition method is corrected and existence of the artifacts is determined, and precise and accurate diagnostic images and images needed for researchers can be acquired by improving quality of spectrum, as well as quality of image.

In addition, quantitative evaluation of a metabolite mimicking a brain is performed, and quantified chemical analysis can also be performed accurately.

In addition, reliability of a radiology diagnosis region in a medical facility can be improved and temporal efficiency can be enhanced by utilizing the system of the present invention for a human magnetic resonance imaging equipment of an ultrahigh field (7.0 Tesla or higher) in the future.

In order to numerically prove the effects of the system proposed in the present invention, the efficiency is proved using the following mathematical expression.

$$C_{mb} = C_{cp} \times (S_{mp}/S_{cp}) \times (f_{T1cp}/f_{T1mp}) \times (f_{T2cp}/f_{T2mp}) \times (N_{cp}/N_{mp})$$   Mathematical expression 1

In the mathematical expression 1, $C_{mb}$ denotes concentration of a human brain metabolite, $C_{cp}$ denotes concentration of a metabolite in an inner container inserted into the coil, $S_{mp}$ denotes a peak area of a human brain metabolite, $S_{cp}$ denotes a peak area in an inner container inserted into the coil, $f_{T1mp}$ denotes T1 relaxation time of a human brain metabolite, $f_{T1cp}$ denotes T1 relaxation time of each metabolite in an inner container inserted into the coil, $f_{T2mp}$ denotes T2 relaxation time of a human brain metabolite, $f_{T2cp}$ denotes T2 relaxation time of each metabolite in an inner container inserted into the coil, $N_{mp}$ denotes the number of transients acquired in a voxel for acquiring a human brain metabolite, and $N_{cp}$ denotes the number of transients acquired in each voxel in an inner container inserted into the coil.

According to the external standard reference system 10 of a type inserted into the coil of a human magnetic resonance imaging equipment of the present invention, an absolute concentration of a metabolite can be obtained according to the mathematical expression 1 by comparing and calculating a brain metabolite solution and metabolites of a human brain.

That is, since a metabolite solution closest to the coil and closest to the brain is selected to compare and calculate a brain metabolite, an error and an error range can be minimized, and diagnosis can be performed using an absolute concentration, not a relative concentration.

In addition, total six inner containers are formed in the mathematical expression 1 so that concentration of a brain metabolite can be changed, and an effect of enhancing intensity of peaks of a metabolite while enhancing sensitivity is expected by adding a brain metabolite (e.g., 12.5 mM of N-acetyl-aspartate [NAA], 12.5 mM of glutamate [Glu], 10 mM of creatine [Cr], 7.5 mM of myo-Inositol [mIns], 5.0 mM of lactate [Lac] and 3.0 mM of choline [Cho]) in the cylindrical inner containers to be close to inside of a coil.

In addition, a cradle is arranged in each of the inner containers and the coil in a space about 10 cm high at the position of the cervical vertebral part, and the cradle is designed based on a thickness, a length and a width optimized to the size of a human brain.

In addition, the present invention is manufactured to enhance uniformity of an image while enhancing intensity of peaks of a brain metabolite and to enhance precision and temporal efficiency.

In addition, cylindrical inner containers capable of optimizing a size and a position of a voxel are inserted focusing on a single voxel spectroscopy technique, and this may have an effect of minimizing influence of artifacts or eliminating the artifacts.

Here, the inner containers 200 are positioned in the direction of 0, 45, 90, 135, 180, 225 and 315 degrees, and total six inner containers are arranged to be positioned 155 mm apart from a coil center of the outer container 100.

The inner container 200 may adjust the amounts of solutions and metabolites (mol concentration) and implement a desired signal when a spectrum is acquired using magnetic resonance spectroscopy and has an effect of performing an accurate quantitative evaluation of concentration.

Accordingly, since the external standard reference system of a type inserted into the coil of a human magnetic resonance imaging equipment according to the present invention quantitatively acquires a brain metabolite and, furthermore, simultaneously acquires the evaluation and analysis functions while minimizing artifacts by selecting an accurate voxel position when a spectrum is acquired using magnetic resonance spectroscopy, there is an effect of acquiring the evaluation and analysis functions in a short time and improving diagnostic reliability of the spectroscopy.

As mentioned in the foregoing description, the detailed description for the preferred embodiments of the present invention are provided to be implemented and embodied by those skilled in the art. While the present invention has been described and illustrated herein with reference to the preferred embodiments thereof, it will be apparent to those skilled in the art that various modifications and variations can be made therein without departing from the spirit and scope of the invention. For instance, the respective configurations disclosed in the aforesaid embodiments of the present invention can be used by those skilled in the art in a manner of being combined with one another. Therefore, the present invention is non-limited by the embodiments disclosed herein, and it is intended to give the present invention a broadest scope matching the principles and new features disclosed herein.

The present invention may be embodied in other specific forms without departing from the spirit and essential characteristics of the present invention. Therefore, the detailed description is to be considered in all respects to be illustrative. The scope of the invention should be determined by reasonable interpretation of the appended claims, and all modifications within equivalent ranges of the present invention are included in the scope of the present invention. In addition, the present invention may be embodied by a combination of claims which do not have an explicit cited relation in the appended claims or may include new claims by amendment after application.

What is claimed is:

1. An external standard reference structure insertable into magnetic resonance imaging equipment for evaluating performance of magnetic resonance spectroscopy, the structure comprising:
    an outer container comprising an opening and a plurality of holes surrounding the opening, the opening to receive a head of an object; and
    a plurality of inner containers insertable into the plurality of holes respectively, the inner containers capable of being filled with metabolites that are different from each other in at least a type or a concentration;
    wherein performance of the magnetic resonance spectroscopy is capable of being evaluated via the magnetic resonance imaging equipment using the structure in association with a following mathematical expression, $$Cmb = Ccp \times (Smp/Scp) \times (fT1cp/fT1mp) \times (fT2cp/fT2mp) \times (Ncp/Nmp), \text{ wherein}$$

Cmb denotes concentration of a human brain metabolite, Ccp denotes concentration of a metabolite, Smp denotes a peak area of a brain metabolite, Scp denotes a peak area in an inner container, fT1mp denotes T1 relaxation time of a brain metabolite, fT1cp denotes T1 relaxation time of a metabolite in an inner container, fT2mp denotes T2 relaxation time of a brain metabolite, fT2cp denotes T2 relaxation time of a metabolite in an inner container, Nmp denotes the number of transients acquired in a voxel for acquiring a brain metabolite, and Ncp denotes the number of transients acquired in each voxel in an inner container.

2. The structure according to claim 1, wherein vertical lengths of at least some of the plurality of inner containers are different from each other.

3. The structure according to claim 1, wherein the inner containers are filled with the metabolites.

4. The structure according to claim 3, wherein the metabolites are different from each other in at least the type or the concentration.

5. The structure according to claim 3, wherein the type and the concentration of at least some of the metabolites filled in the plurality of inner containers are replaceable.

6. The structure according to claim 1, wherein the plurality of inner containers is six.

7. The structure according to claim 1, wherein each of the inner containers is filled with metabolites comprising 12.5 mM of N-acetyl-aspartate [NAA], 12.5 mM of glutamate [Glu], 10 mM of creatine [Cr], 7.5 mM of myo-Inositol [mIns], 5.0 mM of lactate [Lac], and 3.0 mM of choline [Cho].

8. The structure according to claim 1, wherein the outer container is configured to receive a coil in association with an inside surface of the opening of the outer container or an outside surface of the outer container surrounding the plurality of holes.

9. A system to evaluate performance of magnetic resonance spectroscopy, the system comprising:
    an external standard reference structure comprising:
        an outer container having an opening and a plurality of holes surrounding the opening, the opening to receive a head of an object; and
        a plurality of inner containers insertable into the plurality of holes respectively, the inner containers capable of being filled with metabolites that are different from each other in at least a type or a concentration; and
    magnetic resonance imaging equipment into which the external standard reference structure is capable of being inserted to evaluate the performance of magnetic resonance spectroscopy using the external standard reference structure in association with a following mathematical expression, $$C_{mb} = C_{cp} \times (S_{mp}/S_{cp}) \times (f_{T1cp}/f_{T1mp}) \times (f_{T2cp}/f_{T2mp}) \times (N_{cp}/N_{mp}), \text{ wherein}$$

$C_{mb}$ denotes concentration of a human brain metabolite, $C_{cp}$ denotes concentration of a metabolite, $S_{mp}$ denotes a peak area of a brain metabolite, $S_{cp}$ denotes a peak area in an inner container, $f_{T1mp}$ denotes T1 relaxation time of a brain metabolite, $f_{T1cp}$ denotes T1 relaxation time of a metabolite in an inner container, $f_{T2mp}$ denotes T2 relaxation time of a brain metabolite, $f_{T2cp}$ denotes T2 relaxation time of a metabolite in an inner container, $N_{mp}$ denotes the number of transients acquired in a voxel for acquiring a brain metabolite, and $N_{cp}$ denotes the number of transients acquired in each voxel in an inner container.

10. The system according to claim 9, wherein vertical lengths of at least some of the plurality of inner containers are different from each other.

11. The system according to claim 9, wherein the inner containers are filled with the metabolites.

12. The system according to claim 11, wherein the metabolites are different from each other in at least the type or the concentration.

13. The system according to claim 11, wherein the type and the concentration of at least some of the metabolites filled in the plurality of inner containers are replaceable.

14. The system according to claim 9, wherein the plurality of inner containers is six.

15. The system according to claim 9, wherein each of the inner containers is filled with metabolites comprising 12.5 mM of N-acetyl-aspartate [NAA], 12.5 mM of glutamate [Glu], 10 mM of creatine [Cr], 7.5 mM of myo-Inositol [mIns], 5.0 mM of lactate [Lac], and 3.0 mM of choline [Cho].

16. The system according to claim 9, wherein the outer container is configured to receive a coil in association with an inside surface of the opening of the outer container or an outside surface of the outer container surrounding the plurality of holes.

* * * * *